United States Patent [19]

Kafri et al.

[11] Patent Number: 4,854,708
[45] Date of Patent: Aug. 8, 1989

[54] OPTICAL EXAMINATION APPARATUS PARTICULARLY USEFUL AS A FIZEAU INTERFEROMETER AND SCHLIEREN DEVICE

[75] Inventors: Oded Kafri, Beersheva; Kathi M. Kreske, Petah Tikva, both of Israel

[73] Assignee: Rotlex Optics Ltd., BeerSheba, Israel

[21] Appl. No.: 123,671

[22] Filed: Nov. 23, 1987

[51] Int. Cl.$^4$ .............................................. G01B 9/02
[52] U.S. Cl. ...................................... 356/359; 356/73; 356/371
[58] Field of Search .................. 356/359, 360, 371, 73

[56] References Cited

U.S. PATENT DOCUMENTS 3,815,998 6/1974 Tietze .................................. 356/371

OTHER PUBLICATIONS

Dukhopel, "Interference Methods and Instruments for Inspecting Optical Flats" *Sov. J. Opt. Tech.*, vol. 38, No. 9, pp. 570–578, 9/71.
Krasouskii et al., "The Sensitivity Threshold of an Auto Collimation Television Shadow Graph" *Sov. J. Opt. Tech.*, vol. 41, No. 9, pp. 406–409, 9/74.
Marchant et al., "A Large Interferometer for the Examination of Aircraft Camera Window" *Opt. & Laser Tech.*, pp. 158–160, 8/77.

*Primary Examiner*—Davis I. Willis
*Assistant Examiner*—Matthew W. Koren
*Attorney, Agent, or Firm*—Benjamin J. Barish

[57] ABSTRACT

Optical examination apparatus is described including a basic setup comprising a point source of light, a first optical system forming a converging beam of light reflected from the examined object, and a second optical system located to receive the intercepted beam of reflected light, to collimate it, and to direct the collimated beam to a viewing device. The basic setup is capable of combined operation as a Fizeau interferometer, a schlieren device, and/or a moire deflectometer.

13 Claims, 5 Drawing Sheets

The Fizeau Interferometer

Fig. 1  The basic telescope setup

Fig. 2  The moiré deflectometer

Fig. 3  The Fizeau Interferometer

Fig. 4  The schlieren setup

OPTICAL EXAMINATION APPARATUS PARTICULARLY USEFUL AS A FIZEAU INTERFEROMETER AND SCHLIEREN DEVICE

RELATED APPLICATION

The present application is related to application Ser. No. 154,469, field Feb. 8, 1988, now U.S. Pat. No. 4,810,895, which is a continuation of application Ser. No. 07/003,055 filed Jan. 13, 1987 (now abandoned) by Oded Kafri and Ilana Glatt, and assigned to the same assignee as the present application.

BACKGROUND OF THE INVENTION

The above-cited patent application Ser. No. 07/154,469 relates to a method and apparatus for optional examination of an object, particularly by moire ray deflection mapping. The present application is directed to the extension of the basic setup described in that patent application so as to enable the apparatus also to operate as a Fizeau interferometer and also as a schlieren device, as well as a moire ray deflection mapper.

There are two different approaches to optical metrology, namely: interferometry, which measures phase retardation between two light beams, and ray-deflection analysis. The latter was first utilized in schlieren photography, and later in schlieren interferometry and moire deflectometry. patent application Ser. No. 07/154,469 describes an instrument which operates as a moire deflectometer. The invention of the present application shows how the basic telescopic instrument of that patent application can be used to produce an instrument which can operate independently not only as a moire deflectometer, but also as a Fizeau interferometer or as a schlieren device. As will be described more particularly below, such an instrument can be used in all three modes of operation without moving any optical components, and therefore offers a unique opportunity to compare the three methods. Moreover, the basic instrument can be used to operate according to all three methods simultaneously, and therefore the combinations of Fizeau and moire, moire and schlieren, and Fizeau and schlieren, can complement each other to produce improved results.

More particularly, the above-cited application Ser. No. 07/154,469 discloses a method, and also apparatus, for optical examination of an object involving the steps: providing a point source of light producing a diverging beam of direct light; directing the diverging beam of direct light to a first optical system including the object to be examined, which system retraces the light in the form of a beam of reflected light from the examined object back towards the point source of light; intercepting the converging beam of reflected light before reaching the point source of light; passing the intercepted converging beam of reflected light through a second optical system which collimates the beam of reflected light; and examining the collimated beam of reflected light. That patent application describes the use of the method for moire ray deflection mapping, wherein the examination of the collimated beam of reflected light is effected by directing the collimated beam through first and second gratings at a preselected angular orientation and distance with respect to each other to produce moire fringe patterns providing an indication of the properties of the examined object.

BRIEF SUMMARY OF THE PRESENT INVENTION

As indicated earlier, the invention of the present application may be used for extending the basic setup described in patent application Ser. No. 07/154,469 so as not only to operate as a moire deflectometer, but also to operate as a Fizeau interferometer, or as a schlieren device.

According to the present invention, the first optical system in the setup described above includes a partial transmittance reference plate, whereby a contour map of the object topography is obtained from the interference between the direct light beam and the reflected light beam.

The second optical system includes a schlieren filter, such as a knife-edge spatial filter or any other spatial filter, at the focal point of the reflected beam to cut down the Fourier transform of the image, whereby a schlieren image is produced at the viewing device. The apparatus further includes means for selectively locating the partial transmittance reference plate or the schlieren filter in its respective position in the first and second optical systems.

Further features and advantages of the invention will be apparent from the description below.

BRIEF DESCRIPTION OF THE DRAWINGS

The invention is herein described, by way of example only, with reference to the accompanying drawings, wherein.

Figure 1:
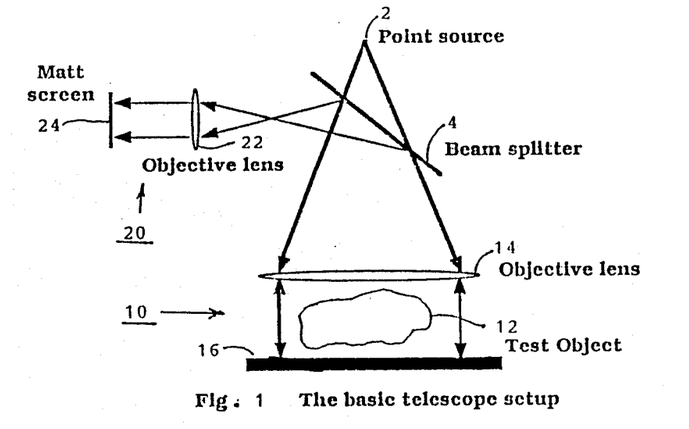
FIG. 1 illustrates the basic telescope setup used in the apparatus of the above-cited application Ser. No. 0./154,469, and also used in the invention of the present application.

DESCRIPTION OF PREFERRED EMBODIMENTS Basic Telescope Setup of FIG. 1

FIG. 1 illustrates the basic telescope setup for examining phase objects. As described in application Ser. 07/154,469, the same basic setup can be used, with minor modification, also for examining specular objects having curved specular surfaces.

The apparatus illustrated in FIG. 1 comprises a point source of light 2 which produces a diverging beam of light., This point source of light 2 may be a laser producing a collimated beam, which is subsequently passed through a divergent lens to produce the diverging beam. The diverging beam passes through a beam splitter 4 and is directed to an optical system, generally designated 10, which includes the phase object to be examined, the latter being designated 12.

Optical system 10 further includes an objective lens 14 which collimates the light from the point source 2 before the light passes through the phase object 12, and a flat reflective surface 16 which reflects the light passing through the phase object 12 back through the phase object to the objective lens 14. The latter lens converges the reflected beam after passing through the phase object 12 and directs back towards the point source 2. Optical system 10, including objective lens 14, the examined phase object 12, and the reflective surface 16, thus causes the light beam, after passing twice through the phase object 12, to be retraced in the form of a converging beam back towards the point source of light 2.

Beam splitter 4 intercepts the converging beam of reflected light before reaching the point source 2 and directs the beam to a second optical system, generally designated 20, including a second objective lens 22. Optical system 20 collimates the beam reflected from beam splitter 4 and directs the collimated beam to a viewing device in the form of a matt screen 24.

Figure 2:
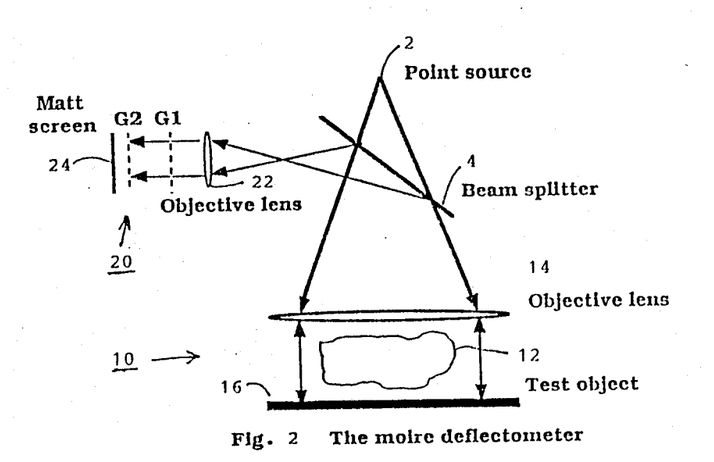
FIG. 2 illustrates the basic setup of FIG. 1 modified to operate as a moire deflectometer, as also described in application Ser. No. 07/154,469, FIGS. 2a–2c illustrating moire fringe patterns produced by the moire deflectometer.

The above-described basic telescope setup illustrated in FIG. 1, together with the setup modified to operate as a moire deflectometer as illustrated in FIG. 2, is described in more detail in application Ser. No. 07/003,055. Thus, to operate the system as a moire deflectometer, optical system 20, after collimating the beam reflected from beam splitter 4, directs the collimated beam through first and second ratings $G_1$, $G_2$, at a preselected angular orientation and distance with respect to each other, to produce moire fringe patterns on the matt screen 24, the matter being attached to grating $G_2$. The moire fringe patterns may be used, according to known techniques, to provide an indication of the properties of the examined phase object 12.

The focal length of optical system 10 is larger than that of optical system 20, thereby reducing the image directed through the first and second gratings $G_1$, $G_2$. This increases the sensitivity. In addition, lens 14 in optical system 10 may be mounted so as to be movable towards and away from the examined phase object 12, to maintain their axial approximation, thereby enabling the apparatus to be used for short focal-length lenses.

As further described in application Ser. No. 07/154,469, the setup illustrated in FIG. 2 is unlike the classical deflectometer setup where beam expansion is achieved by a reverse telescope, comprising a microscope objective and an off-axis telescope mirror attached to a laser. Rather, the setup illustrated in FIG. 2 uses a Newtonian-type telescope, like the Fizeau interferometer. After the laser beam is expanded to the required width and has passed through the large objective lens 14, it passes through the phase object 12 (assuming that it remains parallel with the paraxial approximation), and is then reflected back into the telescope by the flat mirror 16, thus passing twice through the phase object. The retraced beam is diverted 90° by beam splitter 4 to the smaller objective lens 14 where it is recollimated. Now, a small diameter deflectometer may be used to detect redeflections.

As further described in patent application Ser. No. 07/154,469 the setup illustrated in FIG. 2 can be easily modified to measure flat specular objects simply by replacing the flat reflector by the object to be examined. The optical system including the examined object may also include a large objective lens, corresponding to lens 14 in FIGS. 1 and 2, but this is not essential in a setup for examining a concave specular object.

Further information concerning the structure of the moire deflectometer illustrated in FIG. 2, including its mode of operation and results produced, are set forth in application Ser. No. 07/154,469.

The Basic Setup used as a Fizeau Interferometer

Figure 3:
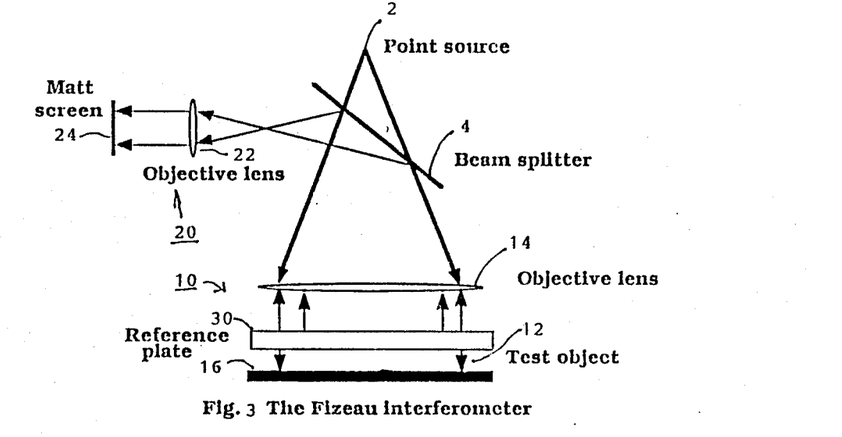
FIG. 3 illustrates the basic setup of FIG. 1 modified to operate as a Fizeau interferometer, FIGS. 3a–3c illustrating the patterns produced when so operated.

FIG. 3 illustrates the basic setup of FIG. 1 modified so as to operate as a Fizeau interferometer. This may be done merely by adding a partial transmittance reference plate 30 to the optical system 10 in the basic setup of FIG. 1. A contour map of the object topography is thus obtained from the interference between the reflected beam and the direct beam. Each fringe represents a change of elevation of one-half wavelength ($\lambda/2$). When testing a phase object 12, it is placed between the reference plate 30 and the reflector surface 16, and a contour map of the optical path will be obtained instead of the height contour map.

It will thus be seen that by simply adding the partial transmittance reference plate 30 to optical system 10, the basic setup of FIG. 1 is converted for use as a Fizeau interferometer. However, when so operated, the following considerations should be noted:

1. The height contour map is highly sensitive to the tilt of the test object. If the slope of the object relative to the reference plate is changed, a different contour map is obtained. Therefore, one must calculate the derivatives which are not affected by a constant slope.

2. The ability to distinguish between hills and valleys is also a problem. A contour map cannot detemine whether the fringes represent increased, decreased, or equal elevation. This must be determined by mechanically shifting the object and observing the relative movement of the fringes.

3. The reference plate and the test object (and the mirror for phase objects) must be stable within $\lambda/10$ during the measurement time. This condition mandates the use of vibration isolated tables when working in an industrial environment.

4. Because of the laser coherence length, the test object must be placed close to the reference plate in order to obtain good quality fringes. This might not be so easy in large phase objects because the object is placed between the reference plate and the mirror. Moreover, the reflectivity of the test object and the reference plate must be similar in intensity.

The main advantage of interferometry is its high sensitivity which results in the ability to measure very small deviations. Unfortunately, this high sensitivity also results in an inability to analyze results from relatively large (compared to $\lambda$) deviations.

Figure 3A:
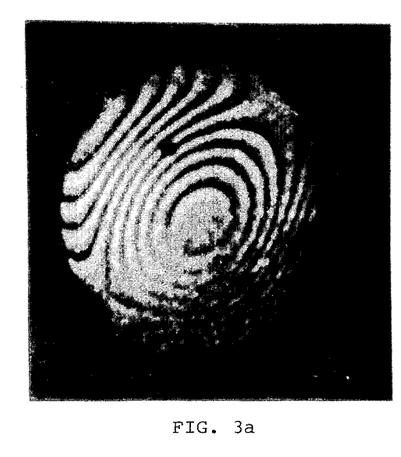
Figure 3B:
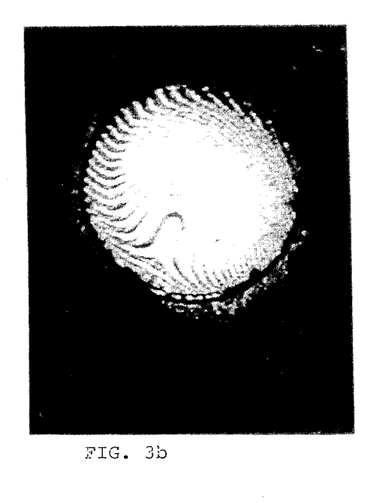
Figure 3C:
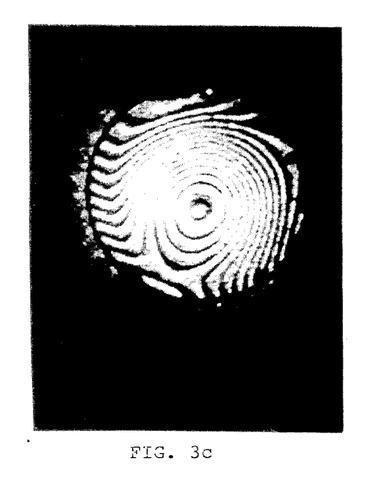

The first object tested was a moderate quality beam splitter, and the contour map obtained by the Fizeau interferometer is shown in FIG. 3a. A second beam splitter contained relatively large slopes, and a complete mapping was unobtainable. A slight tilt of the object exhibited a completely different mapping, as shown in FIGS. 3b and 3c, and reproducing the results was difficult.

Figure 4:
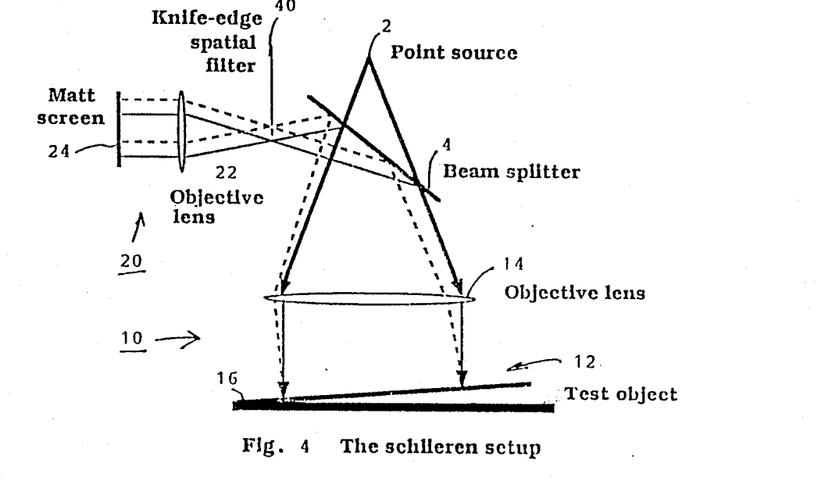
FIG. 4 illustrates the basic setup of FIG. 1 modified to operate as a schlieren device, FIGS. 4a, 4b, illustrating the patterns produced when so operated.

Basic Setup Operated as a Schlieren Device (FIG. 4)

The conventional schlieren technique is a semi-quantitative one. The basic setup illustrated in FIG. 1 can be altered so as to operate as a schlieren device by placing a knife-edge spatial filter, or any other spatial filter, at the focal point of the reflected beam. This spatial filter simply cuts the Fourier transform of the image.

Thus, as shown in FIG. 4, the illustrated schlieren device includes the basic setup illustrated in FIG. 1, but with the addition of a knife-edge spatial filter 40 in the second optical system 20 between the beam splitter 4 and the objective lens 22. Ignoring diffraction effects, if the test object is flat the reflected beam will remain collimated, and all of the rays will be focussed to a infinitely small point. If the object contains gradients in the X-direction, some rays will be focussed below or above the focal point 40. To determine the slopes in the Y-direction, either the object or the knife-edge must be rotated by 90°.

The knife-edge filter 40 causes the image to appear brighter or darker depending the direction of the gradient. The relative magnitudes can be estimated by slowly bringing the knife-edge towards the focal point and observing when an area becomes dark. Hills and valleys can be distinguished in that the first areas to become dark will be the positive gradients, followed by the flat areas, and finally the negative gradients. Exact magnitudes can be determined by precalibrating the knife-edge position to a given gradient of the object. The more quantitative measurement will be sensitive to the tilt of the test object.

Figure 4A:
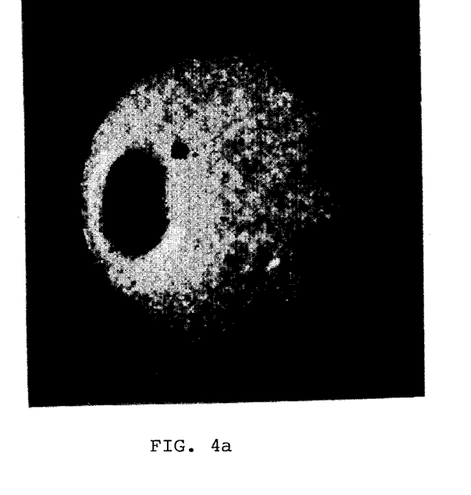
Figure 4B:
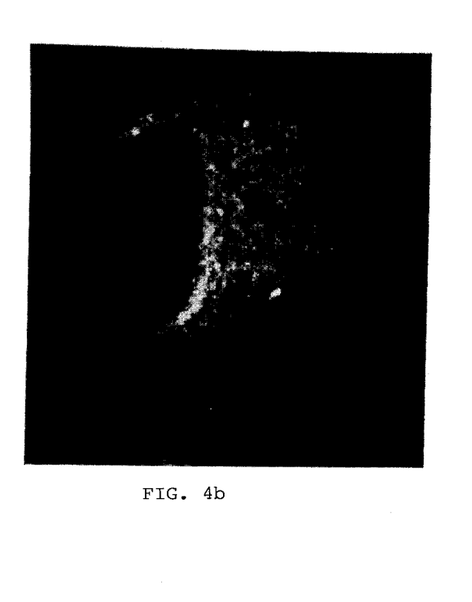

The main disadvantage of the schlieren device is that it is only semi-quantitative, and in order to receive more quantitative measurements the test object alignment becomes a factor. Furthermore, the measurement is dynamical, namely the movement of the knife-edge during the test. Some advantges are the low stability requirement, the easy determination of relative slope, and the high contrast results. FIGS. 4a and 4b illustrate two schlieren photographs of the object of FIG. 3a. In FIG. 4a, the knife-edge cuts a small part of the deflected rays from the Fourier transform of the object. In FIG. 4b, a larger portion of the rays are cut. The high positive slopes of FIG. 3a are detected in FIG. 4a, and in FIG. 4b some smaller slopes are also detected.

Comparison and Combined Operation

As shown above, the operation of the basic telescopic setup may be greatly modified by simple alternations. By inserting a reference plate in the area of the test object, a Frizeau interferometer is achieved; by adding a knife-edge to the focal plane, schlieren setup is obtained; and by placing two Ronchi rulings behind the small objective lens, a moire deflectometer is obtained. Since each of these additions is placed in a different area of the setup, it is possible to apply any combination of the techniques simultaneously. As will be demonstrated, one can benefit from this property. Since it would be desirable to utilize the relative advantages of each method while limiting the disadvantages, the three methods will first be compared.

1. Fringe Interpretation. The basic difference between interferometric techniques which measure phase retardation, and ray delfection techniques such as schlieren and deflectometry, is the quantity which is mapped. Heights are mapped in interferometry and slopes in deflectometry and schlieren. It is true that it is much easier to visualize the shape of an object from a map of height gradients, but this technique is not alway accurate since any small tilt of the object will produce a change in the map of the height gradients. For a field such as flatness analysis (of silicon wafers, hard disks, mirrors, etc.) one would like to map a quantity that is invariant to the tilt of the object and will not map a constant slope. This quantity is the curvature of the fringes, in other words, the second derivitive of the height.

In interferometry, the measured quantity is height contour, and a curved object will produce curved fringes. A finite tilt of the object will change the number of fringes, but not their curavture. Therefore, the analysis is done on the curvature of the fringes. In moire deflectometry a slope contour map is obtained, and a constant slope will cause a change only in the phase of the fringes. In schlieren, as stated earlier, in order to achieve more quantitative results, the position of the knife-edge is precalibrated and therefore affected by a constant tilt of the object. Therefore, because of its invariance to object tilt, deflectometry is preferred.

2. Mechanical Stability Requirement. Moire delfectometry and schlieren photography are ray tracing methods, and the averaging is done at the viewing device. This means that the system stability should be one order of magnitude greater than the required measurement sensitivity. In Fizeau interferometry, the stability requirements depend on the interference phenomenon between two waves. Therefore, no matter what the required sensitivity is, the two interfering beams should be stable within $\lambda/10$. In other words, the refernce plate and the test object must be in unison up to $\lambda/10$ requiring expensive tables and a "laboratory like" environment.

3. Sensitivity. In interferometry, the sensitivity is determined by the light wavelength, The way to calculate the slope is to divide the actual increment between two fringes $\lambda/2$ by the observed distance between them. If one measures the fringe intensity, and we assume that one can resolve $\frac{1}{2}\pi$ of a fringe without imaging processing, we obtain the equation $$\delta\beta = \lambda/4\pi a$$

where $\delta\beta$ is the minimum slope measurement and a is the test object diameter. The minimum sensitivity of moire deflectometry, which is identical to shearing interferometry, is determined by the uncertainty principle $$\delta\phi\delta\chi \geq \lambda/2\pi$$

where $\delta\phi$ is the error in the deflection angle determination and $\delta\chi$ is the spatial resolution. If we substitute $2\delta\beta = \delta\phi$ and $\delta\chi = a$, we obtain the identical result as in interferometry, but the spatial resolution is sacrificed.

In order to receive maximum quality results, a system must be tuned to the appropriate sensitivity. As it was mentioned, the deflectometer can be tuned to the exact desired sensitivity by merely changing the distance between the two gratings. The sensitivity in interferometry can be reduced using a technique called grazing incidence, but this technique is costly compared to its results. The sensitivity in schlieren is similar to that of interferometry and is determined by the micrometer moving the knife-edge.

(a) Combined Operation—Moire and Schlieren

Figure 2A:
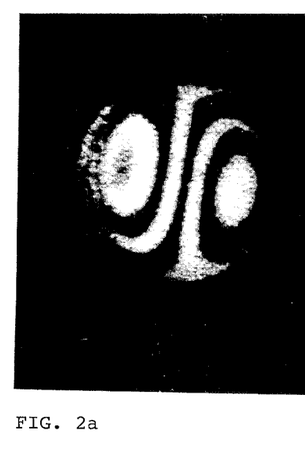
Figure 2B:
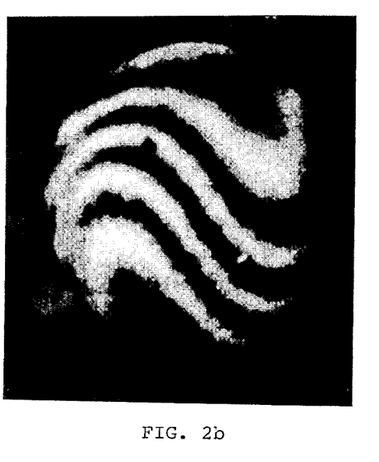

The infinite fringe mode of moire cannot distinguish between hills and valleys, and therefore, it is helpful to add a schlieren device that can easily distinguish between the positive and negative slopes. For example, in the test object of FIGS. 3a and the infinite fringe moire pattern in FIG. 2a, one can see all the slope deviations but cannot determine the signs of the slope. The schlieren device was added, and the first area darkened, which can be seen in FIG. 4a, is the area of the largest positive slope. By moving the knife-edge towards the focal point, additional areas are darkened that follow along the lines of the moire fringes. Therefore while the schlieren device determines relative slopes, the moire infinite fringe mode determines the exact slope increments.

(b) Combined Operation—Interferometry and Moire

Figure 2C:
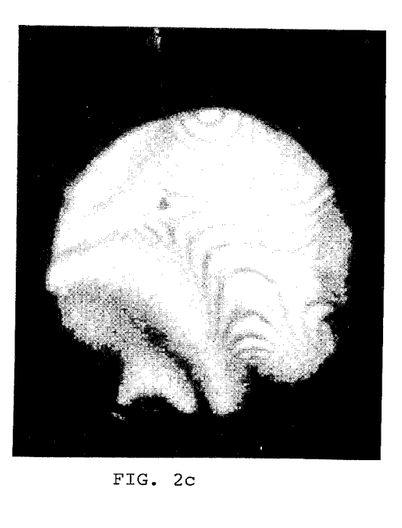

As mentioned earlier, both an advantage and disadvantage of interferometry is its high sensitivity. As seen in FIG. 3b, the areas of relatively small height gradients produce a sensitive contour map. In the areas where the height gradients were relatively large, compared to $\lambda$, a blur of indistinguishable fringes was produced. When combining the infinite fringe moire pattern with interferometry, we achieved a slope contour map in the areas where it was impossible to obtain a height contour map (see FIG. 2c). From this map we now have an idea of what the object looks like in the areas of large height deviations. Although the two sets of fringes are not measuring the same quantities, the moire fringes are only a derivative and therefore it is relatively simple to correlate the results.

(c) Combined Operation—Interferometry and Schlieren

Although in Fizeau interferometry the hills and valleys problem can be solved by a dynamic movement of the object during testing, it is much simpler to apply the schlieren technique and observe the gradual darkening of the object. The schlieren does not follow along the lines of the fringes as in the moire-schlieren combination, rather, since schlieren is the derivative of interferometry, the denser fringes, that represent the highest positive slope, will darken first. These areas are followed by the areas of very few fringes, and lastly, the denser fringes that represent the highest negative slope.

SUMMARY

The above description shows how the basic telescope setup of FIG. 1 may be operated as a moire deflectometer, Fizeau interferometer, schlieren device, and various combinations. Fizeau interferometry was found to be most suitable for high sensitivity measurements of near perfect objects. Deflectometry must be used for objects that require a lower sensitivity analysis, although it can also be used for high sensitivity measurements. Deflectometry is also preferred in flatness analysis where the object tilt will affect the interferometric results. Schlieren is a desirable non-qualitative add on which can determine hills and valleys in a very simple manner without the need to do fringe interpretation (finite fringe deflectometry) or dynamically move the object (interferometry).

The combined operation of deflectometry and interferometry is an ideal solution for analyzing objects with a wide range of slopes. One can utilize the fixed high slopes of interferometry for the areas of the object with relatively small height deviations, and reduced sensitivity moire for the areas of relatively high slopes as was shown in FIG. 2c.

The same instrument of FIG. 1 can also serve as a shearing interferometer by removing the two gratings $G_1$, $G_2$ in FIG. 2, and substituting a shearing device, as known in shearing interferometry. The instrument of FIG. 1 can also serve as a device to determine stress via the photoelastic effect. Linearly polarized laser light combined with a polarized beam splitter will yield high quality fringes representing different levels of stress. This phenomenon is due to the photoelastic effect.

While the invention has been described with respect to one preferred embodiment, it will be appreciated that many other variations, modifications and applications of the invention may be made.

What is claimed is:

1. Optical examination apparatus for determining properties of an object, comprising:
   a point source of light producing a diverging beam of direct light;
   a first optical system located such that, when it includes the object to be examined and receives the beam of direct light, it retraces the light in the form of a converging beam of reflected light from the examined object back towards the point source of light;
   means for intercepting the converging beam of reflected light;
   a viewing device;
   a second optical system located to receive said intercepted beam of reflected light, to collimate it, and to direct the collimated beam to said viewing device;
   said first optical system including a partial transmittance reference plate, whereby a contour map of the object topography is obtained from the interference between the direct light beam and the reflected light beam;
   said second optical system including a schlieren filter at the focal point of the reflected beam to cut down the Fourier transform of the image, whereby a schlieren image is produced at said viewing device;
   and means for selectively locating said partial transmittance reference plate or said schlieren filter in its respective position in said first and second optical systems.

2. The apparatus according to claim 1, wherein said first optical system includes a reflecting surface and an objective lens for collecting the diverging light beam from the point source before passing through the examined object, for reflecting the collimated light beam from said reflecting surface, and for converging the collimated light beam towards said point source of light.

3. The apparatus according to claim 2, including means for supporting the examined object, being a phase object, between the objective lens and said reflecting surface, said light beam thereby being passed twice through the examined object.

4. The apparatus according to claim 2, wherein said reflecting surface is the examined object.

5. The apparatus according to claim 1, wherein said objective lens is mounted for translation towards and away from the point source in order to fulfil the paraxial approximation condition.

6. The apparatus according to claim 1, wherein said intercepting means comprises a beamsplitter.

7. The apparatus according to claim 6, wherein said second optical system comprises an objective lens which collimates the beam received from the beam splitter before directing said beam to said viewing device.

8. The apparatus according to claim 1, wherein the focal length of said first optical system is larger than that of the second optical system to reduce the image directed to said viewing device.

9. The apparatus according to claim 1, wherein said point source of light is a laser producing a collimated beam of light.

10. The apparatus according to claim 1, wherein said schlieren filter is a knife-edge spatial filter.

11. The apparatus according to claim 1, wherein said knife-edge spatial filter is adjustable towards and away from said focal point of the reflected beam.

12. The apparatus according to claim 1, further including first and second gratings at a preselected angular orientation and separation with respect to each other located between said viewing device and said second optical system, such that the second optical system directs the collimated beam of reflected light through said first and second gratings to produce moire ray patterns providing an indication of the properties of the examined object.

13. The apparatus according to claim 12, wherein said second optical system comprises an objective lens which collimates the beam received from the beam splitter before directing said beam through said first and second gratings.

* * * * *